US011588297B2

(12) United States Patent
Smith et al.

(10) Patent No.: US 11,588,297 B2
(45) Date of Patent: Feb. 21, 2023

(54) OPTICAL COMPONENT MOUNTING SYSTEM

(71) Applicant: Alcon Inc., Fribourg (CH)

(72) Inventors: Ronald T. Smith, Irvine, CA (US); Alireza Mirsepassi, Irvine, CA (US); Mark Harrison Farley, Laguna Hills, CA (US)

(73) Assignee: Alcon Inc., Fribourg (CH)

( * ) Notice: Subject to any disclaimer, the term of this patent is extended or adjusted under 35 U.S.C. 154(b) by 214 days.

(21) Appl. No.: 16/884,120

(22) Filed: May 27, 2020

(65) Prior Publication Data

US 2020/0381892 A1    Dec. 3, 2020

Related U.S. Application Data

(60) Provisional application No. 62/853,872, filed on May 29, 2019.

(51) Int. Cl.
*H01S 5/02365* (2021.01)
*F16M 11/04* (2006.01)
(Continued)

(52) U.S. Cl.
CPC ......... *H01S 5/02365* (2021.01); *F16M 11/04* (2013.01); *F16M 11/22* (2013.01); *F16M 13/02* (2013.01); *A61F 9/00821* (2013.01)

(58) Field of Classification Search
CPC .... H01S 5/02365; F16M 11/04; F16M 11/22; F16M 13/02; A61F 9/00821
(Continued)

(56) References Cited

U.S. PATENT DOCUMENTS 6,320,384 B1 * 11/2001 Doty ................ G01R 33/34053
324/322
6,413,589 B1 * 7/2002 Li ........................... C22C 49/14
427/419.7
(Continued)

FOREIGN PATENT DOCUMENTS

CN         111175911 A  *  5/2020  ........... G02B 6/4239
EP         0196875 A1  * 10/1986  ............... G02B 6/42
(Continued)

*Primary Examiner* — Clayton E. LaBalle
*Assistant Examiner* — Kevin C Butler
(74) *Attorney, Agent, or Firm* — Patterson + Sheridan, LLP

(57) ABSTRACT

Devices and methods are disclosed for an optical component mounting system for supporting an optical component such as a laser. The mounting system comprises a first component comprising a first surface, a second component comprising a second surface facing the first surface, and adhesive between the first surface of the first component and the second surface of the second component, wherein the first component comprises at least three mounting pads extending from the first surface for contacting the second surface of the second component and providing direct support between the first component and the second component. The component comprising the mounting pads may be a lower mount, an upper mount such as an upper clamping mount, or a bonding pad or other component in the stack of components. A method of assembling the stack of components may comprise curing the adhesive at a temperature at or above an upper end of an expected temperature operating range for the optical component mounting system.

17 Claims, 3 Drawing Sheets

US 11,588,297 B2

Page 2

(51) Int. Cl.
*F16M 11/22* (2006.01)
*F16M 13/02* (2006.01)
*A61F 9/008* (2006.01)

(58) Field of Classification Search
USPC .......................................................... 372/109
See application file for complete search history.

(56) References Cited

U.S. PATENT DOCUMENTS

| | | | | |
|---|---|---|---|---|
| 6,896,384 | B2 * | 5/2005 | McWhirter | A61F 9/008 |
| | | | | 359/872 |
| 9,468,368 | B2 * | 10/2016 | Smith | G02B 27/00 |
| 9,522,842 | B2 * | 12/2016 | Nonnet | C03C 10/0036 |
| 9,572,629 | B1 * | 2/2017 | Papac | G01J 1/0425 |
| 9,782,063 | B2 | 10/2017 | Bacher | |
| 11,022,765 | B2 * | 6/2021 | Wang | G02B 6/4246 |
| 2008/0131723 | A1 * | 6/2008 | Tucker | B23K 1/0008 |
| | | | | 228/208 |
| 2014/0241665 | A1 * | 8/2014 | Beresnev | G02B 27/30 |
| | | | | 385/33 |
| 2016/0166139 | A1 * | 6/2016 | Bacher | G02B 6/4225 |
| | | | | 600/249 |
| 2017/0075068 | A1 * | 3/2017 | Beresnev | G02B 6/262 |
| 2020/0381892 | A1 * | 12/2020 | Smith | A61B 3/0008 |
| 2021/0286146 | A1 * | 9/2021 | Heidemann | G02B 7/008 |

FOREIGN PATENT DOCUMENTS

| | | | | |
|---|---|---|---|---|
| EP | 1345059 A1 * | 9/2003 | ........... | G02B 6/4236 |
| JP | 2005338862 A * | 12/2005 | ............. | G02B 7/003 |
| JP | 2016517972 A * | 3/2016 | ............... | G02B 6/42 |
| WO | WO-2014181116 A1 * | 11/2014 | ........... | B23K 1/0008 |
| WO | WO-2021158784 A1 * | 8/2021 | ............... | G02B 6/42 |

* cited by examiner

OPTICAL COMPONENT MOUNTING SYSTEM

PRIORITY CLAIM

This application claims the benefit of priority of U.S. Provisional Patent Application Ser. No. 62/853,872 titled "OPTICAL COMPONENT MOUNTING SYSTEM," filed on May 29, 2019, whose inventors are Ronald T. Smith, Alireza Mirsepassi, and Mark Harrison Farley, which is hereby incorporated by reference in its entirety as though fully and completely set forth herein.

TECHNICAL FIELD

The present disclosure is directed to optical component mounting systems, such as laser mounting systems for lasers used in ophthalmic procedures.

BACKGROUND

Lasers are used in many different medical procedures including a number of different ophthalmic procedures. For example, therapeutic lasers are used for photocoagulation of retinal tissue to treat issues such as retinal tears and effects of diabetic retinopathy. In an example of such procedures, the distal end of a laser probe is introduced into the eye globe through a trocar cannula. The laser system can be activated to emit an aiming laser beam, which may be a first color such as red, to show where the laser probe is pointed. When the operator (e.g., an eye surgeon) has the aiming laser beam pointed at the intended spot, the operator then can activate the laser system to emit a therapeutic laser beam, which may be a second color such as green, to the intended spot, or areas around the intended spot, to effect treatment (e.g., photocoagulation).

In certain laser arrangements, light from multiple lasers may be coupled into a single optical fiber. For example, in an arrangement for an ophthalmic procedure as described above, the light emitted from an aiming laser and the light emitted from a therapeutic laser may be coupled together into a single optical fiber for the laser probe. In this way, the beam from the therapeutic laser is aligned to be directed at the same location as the aiming spot.

In these and other related laser arrangements, it is important to precisely align the lasers. For example, it is important to precisely align a laser for coupling the beam of the laser into a fiber core. In addition, in is important that a laser beam remain stable and free from directional drift or other movement once the laser is aligned. It is also important that other optical components, such as beam splitters, lenses, and mirrors, remain mechanically stable. Lasers and other optical components can become misaligned due to external factors such as temperature, humidity, and/or vibration. There is a need for improved optical component mounting systems that allow alignment of a laser or another optical component while maintaining stability of the laser or other optical component and preventing and/or minimizing directional drift of the laser or other optical component once it is aligned.

SUMMARY

The present disclosure is directed to improved designs for optical component mounting systems, such as laser mounting systems for lasers used in ophthalmic procedures. The present disclosure is also directed to methods relating to improved optical component mounting systems.

In some embodiments, an optical component mounting system comprises a stack of components for supporting the optical component, the stack of components comprising: a first component comprising a first surface; a second component comprising a second surface facing the first surface; and adhesive between the first surface of the first component and the second surface of the second component adhering the first component and the second component together; wherein the first component comprises at least three mounting pads extending from the first surface, wherein the mounting pads of the first component contact the second surface of the second component and provide direct support between the first component and the second component.

The first component comprising the at least three mounting pads may be above or below the second component in the stack of components. In one example, the first component is a lower mount and the second component is a lower bonding pad. In another example, the first component is a lower bonding pad and the second component is a lower mount. In another example, the first component is an upper clamping mount and the second component is an upper bonding pad. In another example, the first component is an upper bonding pad and the second component is an upper clamping mount. The optical component may comprise a laser diode or another optical component such as a beam splitter, a lens, or a mirror such as a fold mirror.

In some embodiments, a method of assembling an optical component mounting system comprises the steps of: (i) stacking together a first component and a second component, wherein the first component comprises a first surface, wherein the second component comprises a second surface facing the first surface, wherein the first component comprises at least three mounting pads extending from the first surface, wherein when the first component and the second component are stacked together the mounting pads of the first component contact the second surface of the second component, and wherein the step of stacking together the first component and the second component comprises placing adhesive between the first surface of the first component and the second surface of the second component; and (ii) curing the adhesive at a temperature at or above an upper end of an expected temperature operating range for the optical component mounting system. For example, the step of curing the adhesive may comprise curing the adhesive at or above 35 degrees Celsius. The step of stacking together the first component and the second component may comprise stacking the first component on top of the second component or stacking the second component on top of the first component. The optical component may comprise a laser diode or another optical component such as a beam splitter, a lens, or a mirror such as a fold mirror.

These and other embodiments and their advantages will be appreciated and understood by persons of ordinary skill in the art in view of the description herein and the accompanying drawings.

BRIEF DESCRIPTION OF THE DRAWINGS

The accompanying drawings illustrate implementations of the devices and methods disclosed herein and, together with the description, serve to explain the principles of the present disclosure.

Figure 1:
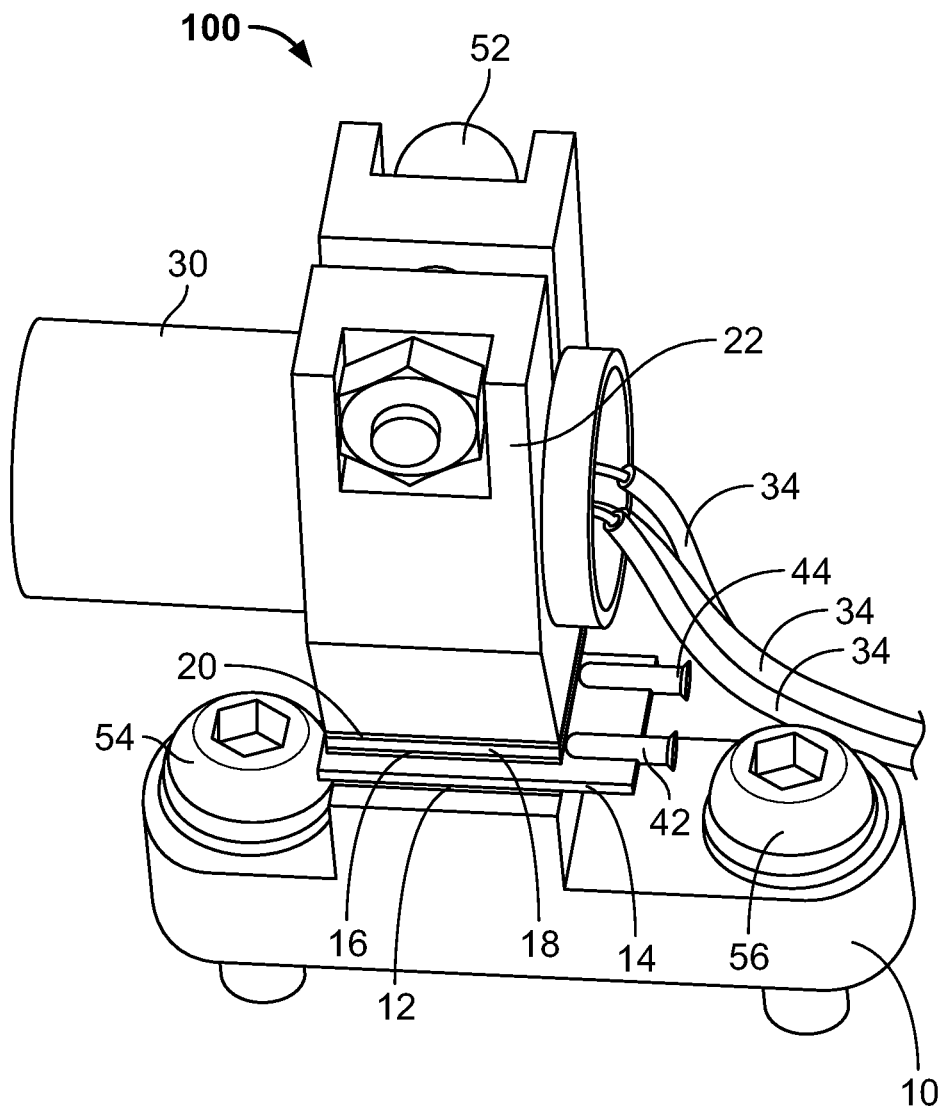
FIG. 1 shows a perspective view of an example of an optical component mounting system in accordance with the present invention, in the form of a laser mounting system.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates. In particular, the features, components, and/or steps described with respect to one implementation may be combined with the features, components, and/or steps described with respect to other implementations of the disclosure. For simplicity, in some instances the same reference numbers are used throughout the drawings to refer to the same or like parts.

FIG. 1 shows a perspective view of an example of an optical component mounting system 100 in accordance with the present invention. In this example, the optical component mounting system 100 is a laser mounting system that is used to align and support a laser diode 30 and to maintain the stability of the laser diode 30 once it is aligned. While FIG. 1 shows a laser diode 30, an optical mounting system such as that shown in FIG. 1 and as illustrated and described herein may also be used to support and maintain the stability of other optical components, such as other lasers, beam splitters, lenses, or mirrors such as fold mirrors.

An optical component mounting system such as laser mounting system 100 may be part of laser system for ophthalmic procedures, which may be a stand-alone laser system or a laser module for an ophthalmic system used for ophthalmic procedures. For example, an optical component mounting system such as laser mounting system 100 may be incorporated into a laser system similar to the PUREPOINT® Vision System of Alcon, headquartered in Fort Worth, Tex., which may be used as a stand-alone laser system or as a laser module for a control console like the control console of the CONSTELLATION® Vision System, also of Alcon.

An optical component mounting system such as laser mounting system 100 may be mounted on an optical plate along with other optical components of the laser system. For example, an optical fiber into which the laser light is to be directed may also be mounted on the optical plate. Electrical lines 34 may be used to supply power to and to control the laser diode 30.

Figure 2:
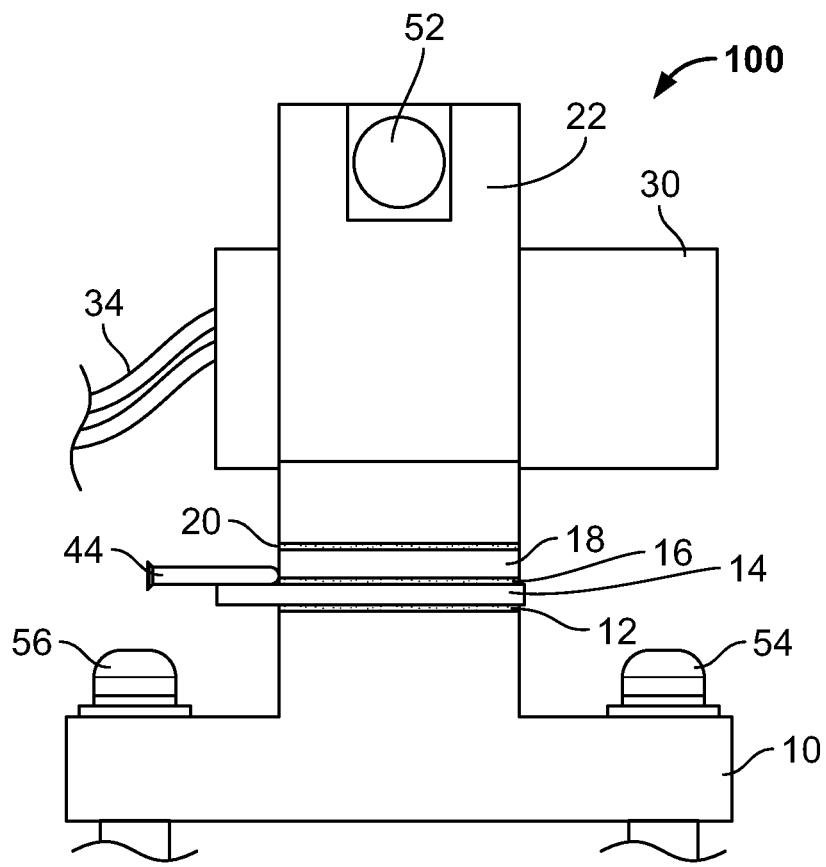
FIG. 2 shows a side view of the laser mounting system of FIG. 1.
Figure 3:
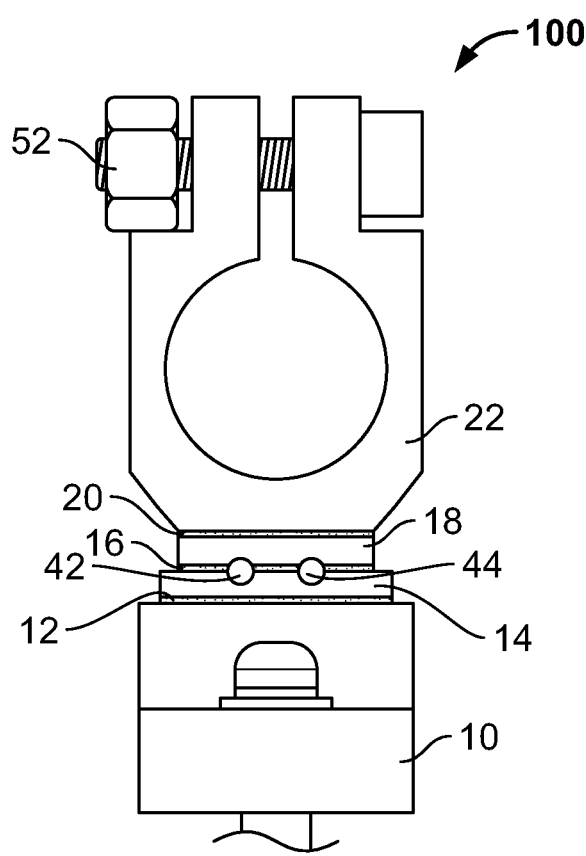
FIG. 3 shows an end view of the laser mounting system of FIG. 1.

As shown in FIGS. 1 through 3, the example optical component mounting system 100 comprises a stack of components that together serve the functions of attaching the laser diode 30 to the optical plate, allowing the position of the laser diode 30 to be adjusted and then fixed, and holding the laser diode 30 in a stable position. At its lower end, the example laser mounting system 100 comprises a lower mount 10 that serves as a base of the stack of components of the laser mounting system 100. The lower mount 10 may be attached to the optical plate by one or more fasteners 54, 56.

At its upper end, the example laser mounting system 100 comprises an upper clamping mount 22 that serves as clamp for holding the laser diode 30. In this example, the upper clamping mount 22 is configured to secure the laser diode 30 between its jaws. One or more fasteners 52 may be loosened to allow the jaws of the upper clamping mount 22 to separate to facilitate placing the laser diode 30 between the jaws, and the one or more fasteners 52 may be tightened to secure the laser diode 30 between the jaws of the upper clamping mount 22.

Between the upper clamping mount 22 and the lower mount 10, the laser mounting system 100 comprises components that allow the position of the laser diode 30 to be adjusted and then, once the desired position (including angular orientation) of the laser diode 30 is attained, fixed in a stable position. These components include a lower bonding part 14 that may be secured to the lower mount 10 by an adhesive 12, an upper bonding part 18 that may be secured to the upper clamping mount 22 by an adhesive 20, and a solder layer 16 between the lower bonding part 14 and the upper bonding part 18. The lower bonding part 14 is located above the lower mount 10, and the upper bonding part 18 is located below the upper clamping mount 22.

The solder layer 16 comprises a solder material that is flowable when heated above a melt temperature but solid and a secure adhesive at lower temperatures including room temperature. Once the stack is assembled, the solder layer 16 is heated to allow adjustment of the position of the laser diode 30. For example, the laser mounting system 100 may include electrical terminals 42, 44 attached to the lower bonding part 14 or the upper bonding part 18, and passing electric current through the electrical terminals 42, 44 causes the bonding part 14 or 18 to which the electrical terminals 42, 44 are attached to become heated. This in turn causes the temperature of the solder layer 16 to rise to a level at which the solder material is flowable, so that the top part of the stack (laser diode 30, upper clamping mount 22, and upper bonding part 18) may be moved relative to the lower part of the stack (lower bonding part 14 and lower mount 10). At this point, a precision instrument (e.g., manipulator) may be used to adjust the position of the top part of the stack (laser diode 30, upper clamping mount 22, and upper bonding part 18) relative to the lower part of the stack (lower bonding part 14 and lower mount 10). The precision instrument may attach to the upper clamping mount 22 or another part of the upper part of the stack and may be used to make fine movements of the upper part of the stack (e.g., both translating and angular movements) until it is in the desired position, e.g., until the laser light emitted from the laser diode 30 is properly directed to the optical fiber core. Once the upper part of the stack is in the desired position, the solder layer 16 is allowed to cool and harden, at which point the position of the upper bonding part 18 relative to the lower bonding part 14 is fixed, and the position of the laser diode 30 is consequently fixed.

Figure 4:
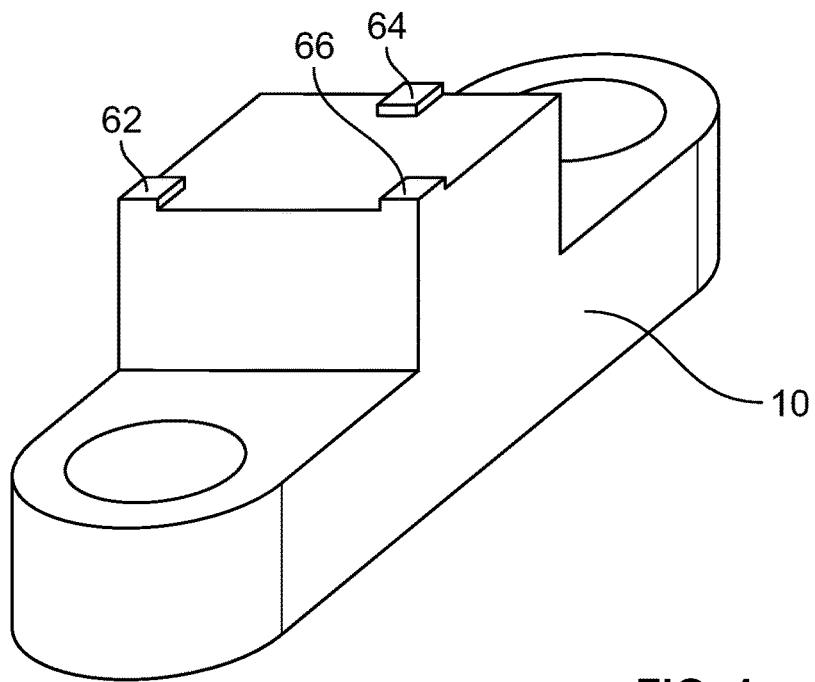
FIG. 4 shows a perspective view of the lower mount of the laser mounting system of FIG. 1.

FIG. 4 shows a perspective view of the lower mount 10 of the laser mounting system 100. As can be seen in FIG. 4, three mounting pads 62, 64, 66 extend from the upper surface of the lower mount 10, which is the surface that faces the lower bonding part 14 when the stack is assembled. When the stack is assembled, the facing surface of the lower bonding part 14 contacts these mounting pads 62, 64, 66, with the adhesive 12 taking up the remaining space between the lower bonding part 14 and the lower mount 10.

As can be seen in FIG. 4, the mounting pads 62, 64, 66 may be arranged in a triangle. In this way, the mounting pads 62, 64, 66 provide three points or areas of contact for the facing surface of the lower bonding part 14, which is flat in this embodiment. Like a tripod, these three points or areas of contact allow for stable support of the lower bonding part 14 (the upper part) on the lower mount 10 (the lower part). At the same time, space is left between the facing surfaces of the lower mount 10 and the lower bonding part 14 so that there is an area for the adhesive 12 for securing the two parts together.

In an alternative arrangement, the upper surface of the lower mount 10 that faces the lower bonding part 14 may be flat, and the facing surface of the lower bonding part 14 may be provided with three mounting pads. Similar to the illustrated embodiment, these three mounting pads provide three points or areas of contact to the facing surface of the lower mount 10. Like a tripod, these three points or areas of contact allow for stable support of the lower bonding part 14 (the upper part) on the lower mount 10 (the lower part). As with the illustrated embodiment, space is left between the facing surfaces of the lower mount 10 and the lower bonding part 14 so that there is an area for the adhesive 12 for securing the two parts together.

Figure 5:
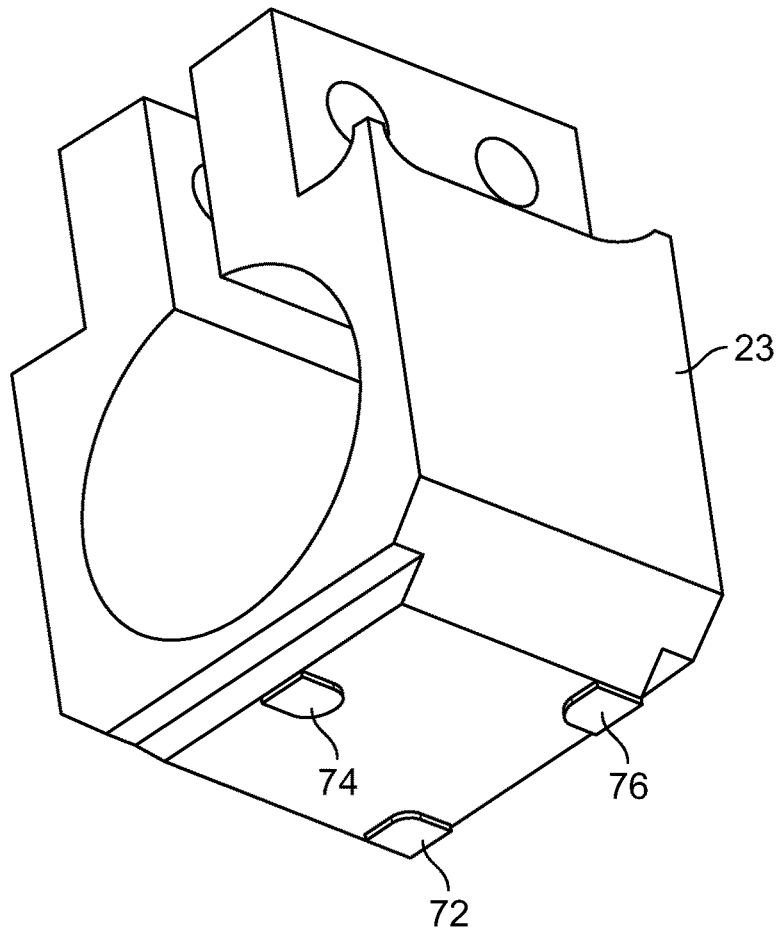
FIG. 5 shows an example of an upper clamping mount for a laser mounting system in accordance with the present invention.

FIG. 5 shows an example of an upper clamping mount 23 for a laser mounting system in accordance with the present invention. The upper clamping mount 23 is similar to the upper clamping mount 22 described with respect to FIGS. 1-3, and can be used as the upper clamping mount in the laser mounting system 100 of FIGS. 1-3 in place of upper clamping mount 22 (with all other parts remaining the same).

As can be seen in FIG. 5, three mounting pads 72, 74, 76 extend from the lower surface of the upper clamping mount 23, which is the surface that faces the upper bonding part 18 when the stack is assembled. Although not visible in FIG. 1, the upper clamping mount 22 may have three mounting pads that extend from the lower surface of the upper clamping mount 22, similar to the mounting pads 72, 74, 76 of FIG. 5. When the stack is assembled, these mounting pads 72, 74, 76 of the upper clamping mount 22 or 23 contact the facing surface of the upper bonding part 18, with the adhesive 20 taking up the remaining space between the upper bonding part 18 and the upper clamping mount 22 or 23.

As can be seen in FIG. 5, similar to the mounting pads 62, 64, 66, the mounting pads 72, 74, 76 may be arranged in a triangle. In this way, the mounting pads 72, 74, 76 provide three points or areas of contact for the facing surface of the upper bonding part 18, which is flat in this embodiment. Like a tripod, these three points or areas of contact allow for stable support of the upper clamping mount 22 or 23 (the upper part) on the upper bonding part 18 (the lower part). At the same time, space is left between the facing surfaces of the upper clamping mount 22 or 23 and the upper bonding part 18 so that there is an area for the adhesive 20 for securing the two parts together.

In an alternative arrangement, the lower surface of the upper clamping mount 22 or 23 that faces the upper bonding part 18 may be flat, and the facing surface of the upper bonding part 18 may be provided with three mounting pads. Similar to the illustrated embodiment, these three mounting pads provide three points or areas of contact to the facing surface of the upper clamping mount 22 or 23. Like a tripod, these three points or areas of contact allow for stable support of the upper clamping mount 22 or 23 (the upper part) on the upper bonding part 18 (the lower part). As with the illustrated embodiment, space is left between the facing surfaces of the upper clamping mount 22 or 23 and the upper bonding part 18 so that there is an area for the adhesive 20 for securing the two parts together.

The embodiments described above with the use of mounting pads as illustrated and described herein provide advantages over prior optical component mounting systems. An optical component mounting system with mounting pads as illustrated and described herein maintains stability of the laser and prevents and/or minimizes drift of the laser or other optical component once it is aligned. In prior optical component mounting systems, lasers or other optical components can become misaligned due to external factors such as temperature, humidity, and/or vibration. This is particularly true where two solid parts are joined by a layer of adhesive with no direct contact between the two solid parts. As external factors such as temperature, humidity, and/or vibration change or are introduced, the adhesive may deform, causing the solid parts to shift position relative to each other. Deformation of the adhesive can also be caused or exacerbated by situations in which the mass is unevenly distributed above the adhesive, which can also cause deformation of the adhesive and shifting of parts. For example, a laser diode mounted as shown in FIG. 1 has more mass on one side of the upper clamping mount than on the other side, causing the mass to be unevenly distributed above the adhesive. Deformation of the adhesive can also be caused or exacerbated by other forces. For example, electrical cables such as those shown in FIG. 1 could cause an upward force on one side of the laser diode, causing uneven loads on the adhesive. An optical component mounting system with mounting pads as illustrated and described herein allows direct contact between solid parts that are joined by adhesive. This direct contact prevents and/or minimizes drift of the laser or other optical component due to changes in the adhesive.

It will be appreciated that the use of three mounting pads allows for three-point contact and stable support of one component on the other. However, in alternative embodiments, more than three mounting pads may be used.

The mounting pads may have any suitable shape for providing the stable support as described herein. In FIG. 4, the mounting pads 62, 64, 66 are shown with a square footprint. These mounting pads 62, 64, 66 have a square flat contact surface for contacting the adjacent component of the stack of components. In FIG. 5, the mounting pads 72, 74, 76 are shown with a footprint having two or three straight sides and one semicircular or curved side. The mounting pads may be shaped to have different contact surfaces or contact points. For example, each mounting pad may have a hemispheric or pyramid shape and may present a single contact point for contacting the adjacent component of the stack of components.

The components with the mounting pads may be manufactured in any suitable manufacturing method. For example, the mounting pads may be manufactured by machining the component. Alternatively, the component with mounting pads may be integrally molded, or mounting pads may be secured to the component.

Any suitable materials may be used for the components of the optical component mounting system. As one example, the upper clamping mount may be made of a ceramic material or fiberglass composite, the lower mount may be made of a ceramic material or fiberglass composite, and the upper and lower bonding parts may be made of ceramic materials capable of withstanding solder temperatures. The upper clamping mount and the lower mount may have low thermal conductivity.

In order to provide additional support in the area of the adhesive, one or more of the adhesive layers in the laser mounting system may include small solid particles within the adhesive, such as spherical glass or sapphire beads. The solid particles (e.g., beads) can have a diameter matching the desired thickness of the layer. In this way, the solid particles maintain the thickness of the layer despite changes in the adhesive, thereby maintaining the positions of the components in the stack and the stability of the laser or other optical component. The solid particles can also minimize thermally-induced expansion of the adhesive layer relative to the adjacent hard components when the assembly gets hot.

In one example of a manufacturing method for an optical component mounting system, a stack of components is assembled together, wherein a first component comprises a first surface, a second component comprises a second surface facing the first surface, and the first component comprises at least three mounting pads extending from the first surface. Adhesive is placed between the first surface of the first component and the second surface of the second component, and the components are stacked together wherein the mounting pads of the first component contact the second surface of the second component. The adhesive is cured at a temperature at or above the upper end of the expected temperature operating range. As one example, if the expected temperature operating range is 10 degrees Celsius to 35 degrees Celsius, the adhesive may be cured at or above 35 degrees Celsius, for example at 40 degrees Celsius. Then, when the optical component mounting system is in use, the system and thus the adhesive will always be at a temperature at or below the temperature at which the adhesive was cured. In this manner, due to thermal effects the adhesive may shrink, but it will not expand beyond its cured volume. Thus, the adhesive will not push the components away from each other due to thermal expansion, and the mounting pads provide direct contact and support between the first component and the second component.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. A laser mounting system for supporting a laser, wherein the laser mounting system comprises a stack of components for supporting the laser, the stack of components comprising:
   a lower mount;
   an upper mount;
   a lower bonding pad;
   an upper bonding pad;
   a solder layer between the lower bonding pad and the upper bonding pad;
   adhesive between the lower mount and the lower bonding pad adhering the lower mount and the lower bonding pad together; and
   adhesive between the upper mount and the upper bonding pad adhering the upper mount and the upper bonding pad together;
   wherein at least one of the components in the stack of components is a first component comprising at least three mounting pads extending toward a second component which is an adjacent component in the stack of components, wherein the mounting pads of the first component contact the second component and provide direct support between the first component and the second component;
   wherein the stack of components further comprises electrical terminals attached to the lower bonding pad or the upper bonding pad such that electric current can be passed through the electrical terminals to cause the lower bonding pad or the upper bonding pad to which the electrical terminals are attached to become heated;
   wherein the heat caused by the electrical current causes a temperature of the solder layer between the lower bonding pad and the upper bonding pad to rise to a level at which a solder material of the solder layer is flowable so that the upper mount and upper bonding pad can be moved relative to the lower mount and lower bonding pad;
   a precision instrument attached to the upper mount to make fine movements of the upper mount until a laser light emitted from a laser diode attached to the upper mount is properly directed to an optical fiber core.

2. A laser mounting system as recited in claim 1, wherein the first component comprising the at least three mounting pads is the lower mount and the second component is the lower bonding pad.

3. A laser mounting system as recited in claim 1, wherein the first component comprising the at least three mounting pads is the lower bonding pad and the second component is the lower mount.

4. A laser mounting system as recited in claim 1, wherein the first component comprising the at least three mounting pads is the upper mount and the second component is the upper bonding pad.

5. A laser mounting system as recited in claim 1, wherein the first component comprising the at least three mounting pads is the upper bonding pad and the second component is the upper mount.

6. A laser mounting system as recited in claim 1, wherein the upper mount is an upper clamping mount.

7. A laser mounting system as recited in claim 1, wherein the laser comprises a laser diode.

8. A method of assembling an optical component mounting system for supporting an optical component, wherein the optical component mounting system comprises a stack of components for supporting the optical component, the method comprising:
   stacking together the stack of components comprising:
      a lower mount;
      a lower bonding pad;
      an upper bonding pad;
      an upper mount; and
      a solder layer between the lower bonding pad and the upper bonding pad;
      wherein at least one of the lower mount, lower bonding pad, upper bonding pad and upper mount is a first component and wherein at least one other of the lower mount, lower bonding pad, upper bonding pad, and upper mount, adjacent to the first component, is a second component, wherein the first component comprises a first surface, wherein the second component comprises a second surface facing the first surface, wherein the first component comprises at least three mounting pads extending from the first surface, wherein when the first component and the second component are stacked together the mounting pads of the first component contact the second surface of the second component;

applying adhesive between the lower mount and the lower bonding pad to adhere the lower mount and the lower bonding pad together;

applying adhesive between the upper mount and the upper bonding pad to adhere the upper mount and the upper bonding pad together;

attaching electrical terminals to the lower bonding pad or the upper bonding pad such that electric current can be passed through the electrical terminals to cause the lower bonding pad or the upper bonding pad to which the electrical terminals are attached to become heated;

wherein the heat caused by the electrical current causes a temperature of the solder layer between the lower bonding pad and the upper bonding pad to rise to a level at which a solder material of the solder layer is flowable so that the upper mount and upper bonding pad can be moved relative to the lower mount and lower bonding pad;

attaching a precision instrument to the upper mount to make fine movements of the upper mount until a laser light emitted from a laser diode attached to the upper mount is properly directed to an optical fiber core;

curing the adhesive at a temperature at or above an upper end of an expected temperature operating range for the optical component mounting system;

discontinuing electric current flow through the solder layer to cool and harden the solder layer.

9. A method of assembling an optical component mounting system as recited in claim 8, wherein the step of curing the adhesive comprises curing the adhesive at or above 35 degrees Celsius.

10. A method of assembling an optical component mounting system as recited in claim 8, wherein the step of stacking together the first component and the second component comprises stacking the first component on top of the second component.

11. A method of assembling an optical component mounting system as recited in claim 8, wherein the step of stacking together the first component and the second component comprises stacking the second component on top of the first component.

12. A method of assembling an optical component mounting system as recited in claim 8, wherein the optical component comprises a laser diode.

13. The method of assembling an optical component mounting system as recited in claim 8, wherein the first component comprising the at least three mounting pads is the lower mount and the second component is the lower bonding pad.

14. The method of assembling an optical component mounting system as recited in claim 8, wherein the first component comprising the at least three mounting pads is the lower bonding; pad and the second component is the lower mount.

15. The method of assembling an optical component mounting system as recited in claim 8, wherein the first component comprising the at least three mounting pads is the upper mount and the second component is the upper bonding pad.

16. The method of assembling an optical component mounting system as recited in claim 8, wherein the first component comprising the at least three mounting pads is the upper bonding pad and the second component is the upper mount.

17. The method of assembling an optical component mounting system as recited in claim 8, wherein the upper mount is an upper clamping mount.

\* \* \* \* \*